United States Patent
Irwin et al.

(10) Patent No.: US 9,913,631 B2
(45) Date of Patent: Mar. 13, 2018

(54) BRUSH SYSTEM FOR A CELL COLLECTING DEVICE

(71) Applicant: Cook Medical Technologies LLC, Bloomington, IN (US)

(72) Inventors: Nate Irwin, Bloomington, IN (US); Triona Campbell, Killaloe (IE)

(73) Assignee: Cook Medical Technologies LLC, Bloomington, IN (US)

( * ) Notice: Subject to any disclaimer, the term of this patent is extended or adjusted under 35 U.S.C. 154(b) by 334 days.

(21) Appl. No.: 14/742,416

(22) Filed: Jun. 17, 2015

(65) Prior Publication Data
US 2015/0366545 A1 Dec. 24, 2015

Related U.S. Application Data (60) Provisional application No. 62/013,972, filed on Jun. 18, 2014.

(51) Int. Cl.
| A61B 5/00 | (2006.01) |
| A61B 10/04 | (2006.01) |
| A61B 10/02 | (2006.01) |

(52) U.S. Cl.
CPC .......... *A61B 10/04* (2013.01); *A61B 10/02* (2013.01); *A61B 2010/0216* (2013.01)

(58) Field of Classification Search
CPC .. A61B 10/02; A61B 10/04; A61B 2010/0216
USPC ........................................................ 600/569
See application file for complete search history.

(56) References Cited

U.S. PATENT DOCUMENTS

| 2,847,990 | A | | 8/1958 | Ayre | |
| 4,245,653 | A | * | 1/1981 | Weaver | A61B 10/0291 600/563 |
| 4,245,663 | A | | 1/1981 | Solowy | |
| 5,738,109 | A | * | 4/1998 | Parasher | A61B 10/02 600/569 |
| 9,055,963 | B2 | * | 6/2015 | Miloslavski | A61B 17/221 |
| 2013/0267824 | A1 | | 10/2013 | Johnson et al. | |

FOREIGN PATENT DOCUMENTS

| WO | WO 2005/079682 A1 | 9/2005 |
| WO | WO 2012/075409 A1 | 6/2012 |

OTHER PUBLICATIONS

International Search Report and Written Opinion for related International Application No. PCT/US2015/036188, dated Nov. 19, 2015 (17 pages).

* cited by examiner

*Primary Examiner* — Max Hindenburg
(74) *Attorney, Agent, or Firm* — Brinks Gilson & Lione (57) ABSTRACT

A cell collection device for collecting cells from the inner surface of a body lumen is disclosed. The cell collection device includes a longitudinal member, a plurality of struts that are expandable radially, and a sheath having an inner surface that constrains the outward movement of the plurality of struts when the sheath is in a first position and does not constrain the outward movement of the plurality of struts when the sheath is in a second position.

22 Claims, 6 Drawing Sheets

BRUSH SYSTEM FOR A CELL COLLECTING DEVICE

FIELD

The present disclosure is related to devices and methods for collecting cell samples in internal organs, and more particularly to devices and methods for collecting cell samples from internal body lumens using a self-expanding cell collection device.

BACKGROUND

It is useful to collect biological surface cells from internal lumens of the body. Such cells are useful for diagnostic procedures including the identification of predictive biomarkers that allow clinicians to predict future prognosis for a patient. In such diagnostic procedures, it is important that a large numbers of cells are collected from an area of interest while minimizing the collection of foreign cells in order to obtain an accurate diagnostic result. Ideally, the collection of the surface cells would occur with no damage to the body lumen.

A current method of collecting surface cells is to use a cytology brush. The cytology brush has stiff bristles that extend radially outward from an axis of the cytology brush, and in some examples the stiff bristles have hooks to retain cell samples. The cytology brush is delivered to the area of interest and then brushed against a surface of the body lumen, abrading cells from the surface and catching the cells within the bristles. The use of the cytology brush may result in bleeding where the lumen surface is abraded and is inefficient in its collection of surface cells. Accordingly, it would be useful to have an alternative to a cytology brush for the collection of surface cells in a body lumen.

SUMMARY

In a first aspect, a cell collection device comprises a longitudinal member, a plurality of struts, a plurality of brushes, and a sheath slidably disposed about the longitudinal member. The longitudinal member has a distal end and a proximal end. The plurality of struts extends member. The plurality of brushes is mounted on the plurality of struts and the sheath has a lumen with an inner diameter and an inner surface facing the longitudinal member. The sheath is movable from a distal position in which the inner surface constrains outward movement of each strut and a proximal position wherein a portion of at least one strut is unconstrained to extend beyond the inner diameter.

In some embodiments, each strut is self-biased to expand a portion of the strut radially. In some embodiments, a portion of each strut of the plurality of struts expands radially in response to an axial compressive force. In some embodiments, each strut of the plurality of struts is a shaft made of a shape memory material having a high energy state when constrained by the inner surface.

In some embodiments, the at least one brush is rotatable about the strut the at least one brush is mounted on.

In some embodiments, the cell collection device further includes a flexible membrane disposed between adjacent struts. In some embodiments, the flexible membrane is a material selected from the group consisting of nylon reinforced polyurethane, silicone, ultra high molecular weight polyethylene, polyethylene terephthalate, polyethylene, and nylon. In some embodiments, the flexible membrane is attached to adjacent struts. In some embodiments, the flexible membrane is attached to adjacent struts between adjacent brushes. In some embodiments, a portion of the flexible membrane extends into at least one brush. In some embodiments, the flexible membrane has at least one cut-out complementary to the plurality of brushes. In some embodiments, a second portion of the flexible membrane opposite the portion extending into the at least one brush does not extend into a brush.

In some embodiments, the cell collection device further includes a distal longitudinal member connected to a distal end of the plurality of struts.

In some embodiments, each strut of the plurality of struts are arranged circumferentially at equal radial spacing about a longitudinal axis.

In some embodiments, the sheath has a side window and the sheath proximal position constrains the outward radial movement of a second plurality of struts from among the plurality of struts and does not constrain the outward radial movement of a third plurality of struts facing the side window. In some embodiments, the cell collection device further includes a second plurality of brushes disposed on the inner surface of the sheath opposing the side window.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present disclosure are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto. Additional advantages will become readily apparent from the following discussion, particularly when taken together with the accompanying drawings.

In the following discussion, the terms "proximal" and "distal" will be used to describe the opposing axial ends of the self-expanding cell collection device, as well as the axial ends of various component features. The term "proximal" is used in its conventional sense to refer to the end of the self-expanding cell collector (or component thereof) that is closest to the operator during use of the self-expanding cell collector. The term "distal" is used in its conventional sense to refer to the end of the self-expanding cell collector (or component thereof) that is initially inserted into the patient, or that is closest to the patient during use. For example, a self-expanding cell collector may have a proximal end and a distal end, with the proximal end designating the end closest to the operator, such as a handle, and the distal end designating an opposite end of the self-expanding cell collector. Similarly, the term "proximally" refers to a direction that is generally towards the operator along the path of the self-expanding cell collector and the term "distally" refers to a direction that is generally away from the operator along the self-expanding cell collector.

Figure 1:
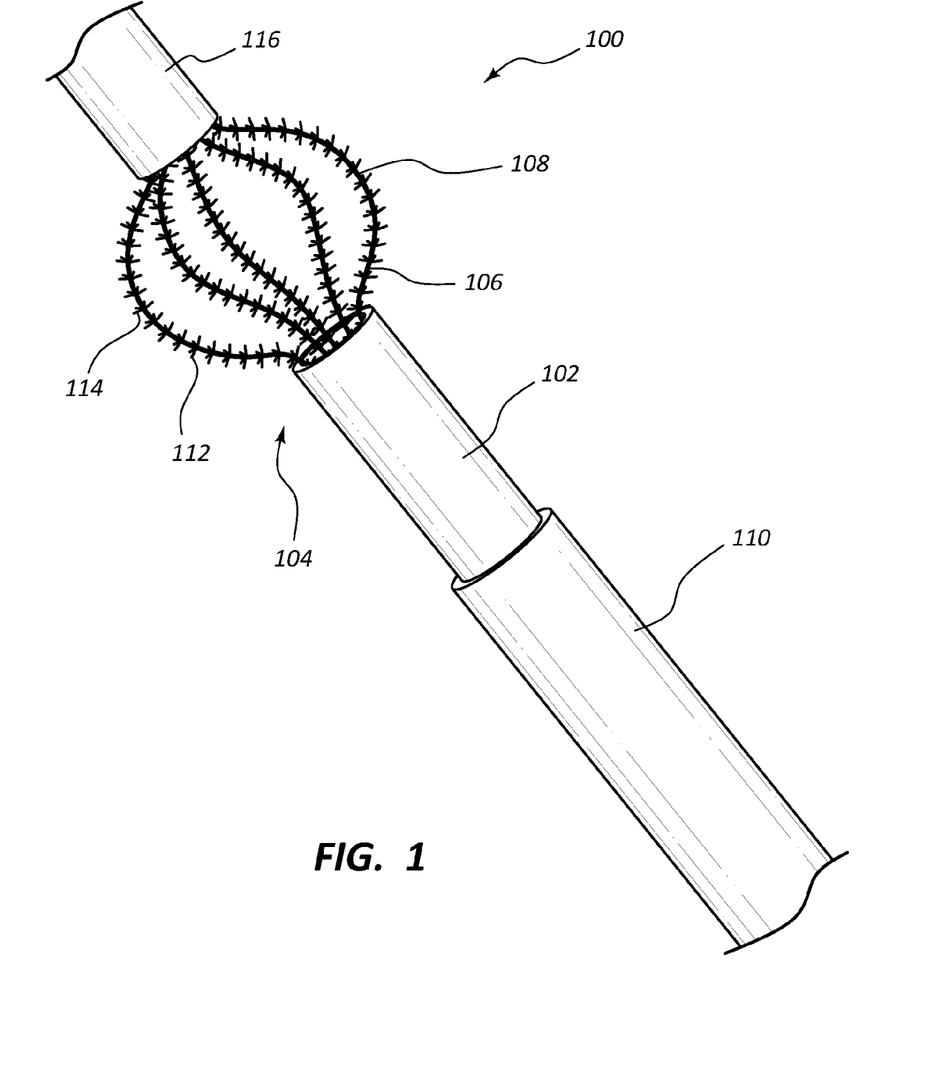
FIG. 1 illustrates a cell collection device in an expanded state.

FIG. 1 illustrates an embodiment of a brush system 100 for cytology applications. The brush system 100 is comprised of a longitudinal member 102 having a distal end 104 and a proximal end (not shown). A plurality of struts 106 extend distally from the distal end 104 of the longitudinal member 102. Each of the plurality of struts 106 may be secured to the distal end 104 of the longitudinal member 102 using conventional techniques such as adhesives, or the plurality of struts 106 may be embedded in a wall of the longitudinal member 102. Each of the plurality of struts 106 has a portion 108 that is expandable in an outward radial direction. In some embodiments, the plurality of struts 106 may be self-biased to expand the portion 108 outward, or in other embodiments the portion 108 may expand in response to an axial compression of the plurality of struts 106. Each of the struts 106 has at least one brush 112 having bristles 114 that extend radially from the strut 106. A sheath 110 is disposed about the longitudinal member 102 and the sheath 110 is configured to slide axially relative to the longitudinal member 102. The sheath 110 has a lumen with an inner surface facing the longitudinal member 102.

In some embodiments, a distal longitudinal member 116 may be connected to a distal end of the plurality of struts 106. The distal longitudinal member 116 may be made of the same material as the longitudinal member 102, or in some embodiments the distal longitudinal member 116 may be made of a material different from the material of the longitudinal member 102. For example, the distal longitudinal member 116 may be made of a softer material than the longitudinal member 102 to reduce trauma to a body lumen. In some embodiments, the distal longitudinal member 116 may be axially movable relative to the longitudinal member 102.

Movement of the distal longitudinal member 116 proximally relative to the longitudinal member 102 compresses the struts 106 axially. The distal longitudinal member 116 may be moved by an operator manipulating a proximal end of the longitudinal member. In some embodiments, the distal longitudinal member 116 may be coupled to a thread or wire (not shown) extending toward the proximal end of the longitudinal member 102 for manipulation by the operator. Tensioning the thread or wire moves the distal longitudinal member 116 towards the longitudinal member 102 compressing the plurality of struts 106. In other embodiments, the distal longitudinal member 116 may have at least a portion extending proximally within the longitudinal member 102. Tensioning the portion extending proximally within the longitudinal member compresses the plurality of struts 106.

The sheath 110 is movable axially from a first position to a second position. In the first position, the inner surface of the sheath 110 covers the plurality of struts 106 and constrains them from moving outward. In the second position shown in FIG. 1, the constraint is removed as the sheath 110 is slid proximally and each of the plurality of struts 106 expands radially. In some embodiments, each of the plurality of struts 106 are self-biased to expand outward and the movement of the sheath 110 to the second position results in the plurality of struts 106 expanding radially. In other embodiments, axial compression of the plurality of struts 106, such as by a thread, will expand a portion of the struts 106 outward when the sheath 110 is moved to the second position. In some embodiments, the sheath 110 extends a majority of the length of the longitudinal member 102 to the proximal end of the longitudinal member 102, such that a movement of the sheath 110 at the proximal end causes a movement of the sheath 110 at the distal end of the longitudinal member 102.

Each of the plurality of struts 106 may be a shaft of a shape memory material such as a nickel titanium alloy. The struts 106 may be self-biased and have a high energy state when constrained by the inner surface of the sheath 110 and a low energy state when the sheath 110 is retracted and the struts 106 are expanded radially.

The brushes 112 may be fixed on the struts 106 so that any movement of the bristles 114 relative to the strut 106 causes a deformation of the bristle 114. For example, the interaction of a bristle 114 brushing a body lumen may cause the bristle 114 to bend as it abrades the surface. In other embodiments, the brushes 112 may be rotatable about the strut 106. In such embodiments the bristles 114 may rotate about the strut 106 when engaging a surface of a body lumen. The rotating bristles 114 may reduce trauma relative to a fixed brush 112. In some embodiments the bristles 114 may be curved to enhance the ability of the bristles 114 to capture cells.

In some embodiments, the brushes 112 may extend the length of the struts 106, or each strut 106 may have a plurality of brushes 112 disposed axially on the strut 106. The plurality of brushes 112 may be disposed at regular intervals, or in other embodiments may have an irregular pattern. Brushes 112 disposed on adjacent struts 106 may have the same pattern, or in some embodiments may have a different pattern that is complementary to a pattern on an adjacent strut 106. For example, in FIG. 5 a first strut 502 has a spacing 504 between adjacent brushes 506 and an adjacent strut 508 may have a brush 510 corresponding to the space 504 between the adjacent brushes 506. Similarly, a space 512 between adjacent brushes 510 on the adjacent strut 508 corresponds to the brushes 506 on the first strut 502.

Figure 2:
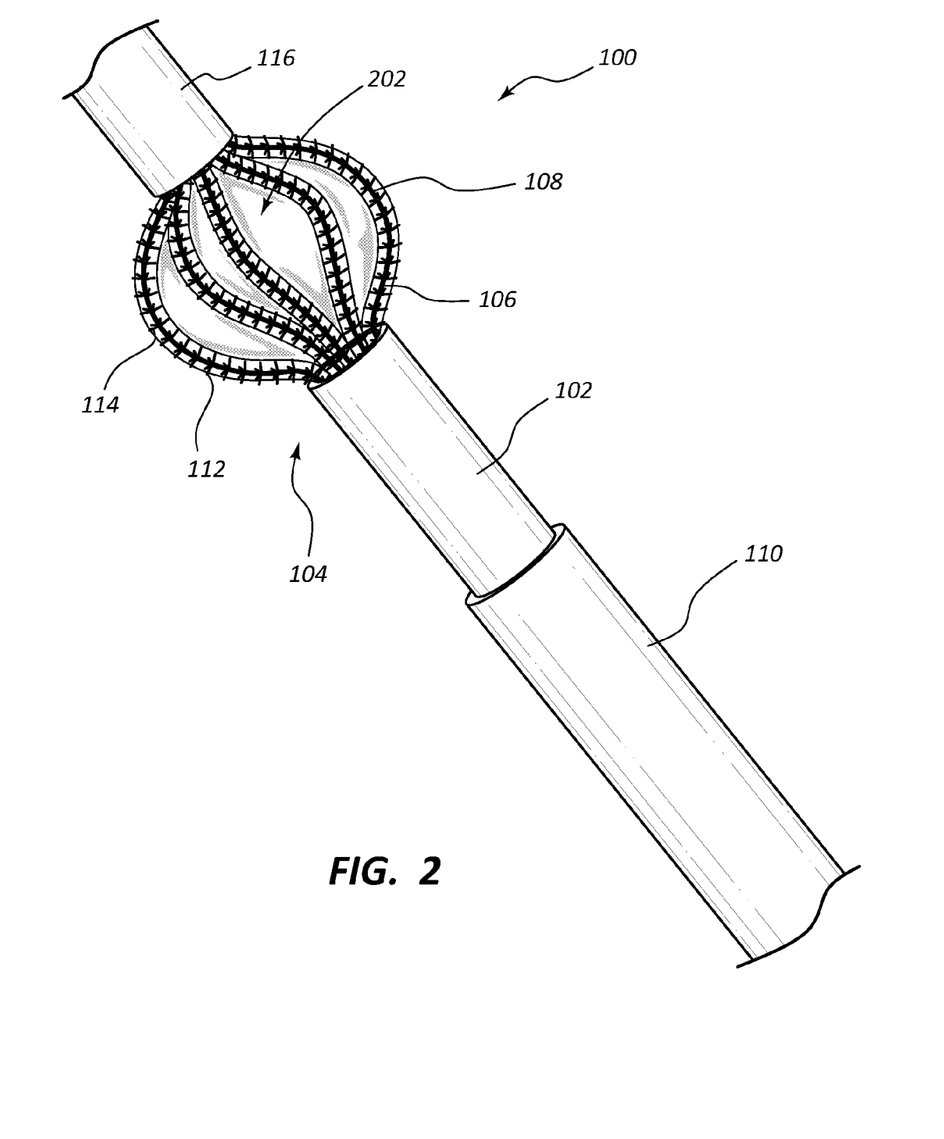
FIG. 2 illustrates a cell collection device having a membrane between adjacent struts.
Figure 3:
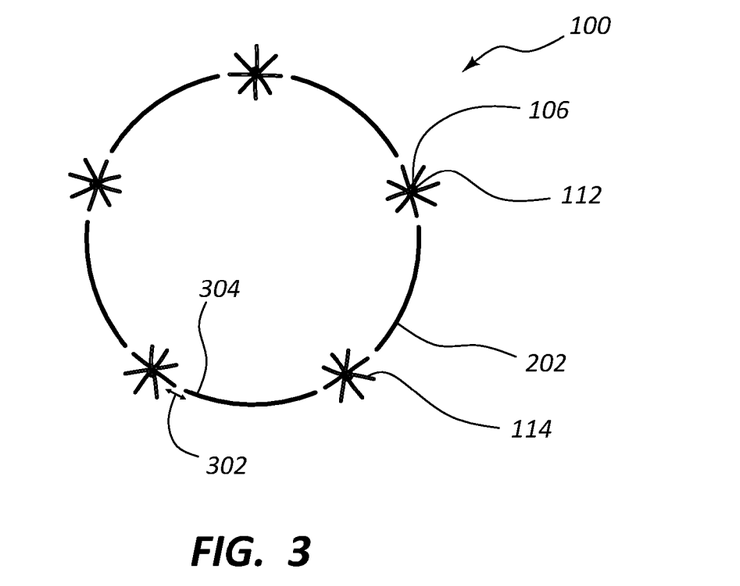
FIG. 3 illustrates a cross-section of the cell collection device of FIG. 2.

FIG. 2 and FIG. 3 illustrate another embodiment of the brush system 100 with a flexible membrane 202 disposed between adjacent struts 106. The flexible membrane 202 may comprises a material such as nylon reinforced polyurethane, silicone, ultra high molecular weight polyethylene, polyethylene terephthalate, polyethylene, and nylon.

FIG. 3 illustrates an axial view of the brush system 100 showing the flexible membrane 202 disposed between adjacent brushes 112. The flexible membrane 202 is shown as extending to the bristles 114 of the brush 112. In some embodiments, the flexible membranes 202 may have a gap 302 between an edge 304 of the flexible membrane 202 and the bristles 114 of the brush 112. The flexible membrane 202 may be attached to the struts 106 adjacent to the brush 112 as shown in FIG. 5.

Figure 4:
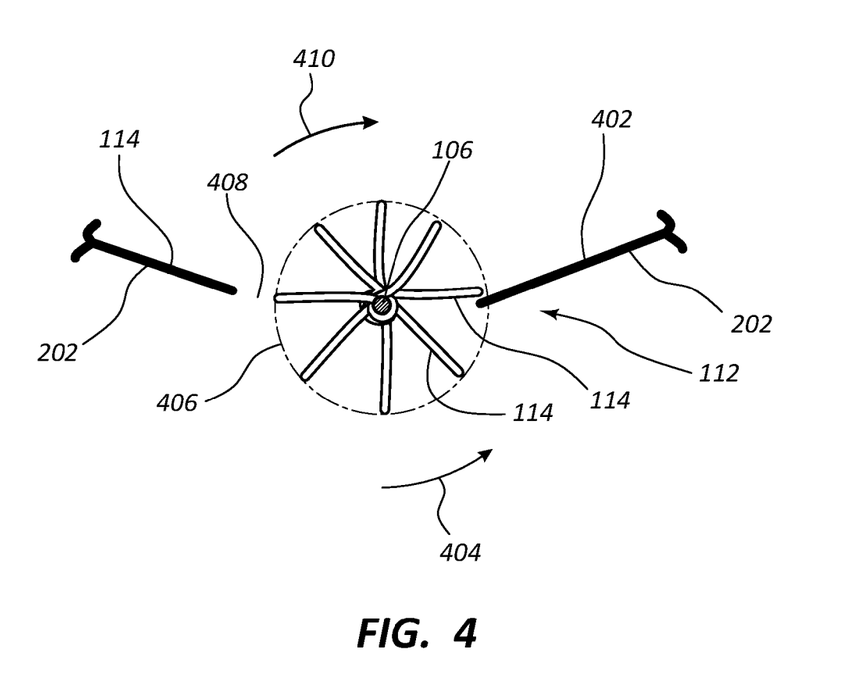
FIG. 4 illustrates a detailed view of a cross-section of a brush from the cell collection device of FIG. 2.

FIG. 4 illustrates a detailed view of the placement of a brush 112 between a first flexible membrane 402 and a second flexible membrane 400. The brush 112 is configured to rotate about the strut 106 with the bristles 114 sweeping a circular shape with a perimeter 406. In this particular example, there is a gap 408 between the second flexible membrane 400 and the perimeter 406 of the swept circle. The first flexible membrane 402 extends beyond the perimeter 406 of the swept circle and into the brush 112.

When the brush system 100 is rotated in a direction indicated by arrow 404 and is in contact with a body lumen, the brush 112 rotates about the strut 106 in the direction indicated by arrow 410. The bristles 114 of the brush 112 collect surface cells as they rub against the body lumen. The collected cells are held in the bristles 114 of the brush 112 as the bristles 114 rotate from the surface of the body lumen into an inner volume of the brush system. The cells may release from the bristles 114 of the brush 112 as the bristles 114 pass into the inner volume, or in the embodiment of FIG. 4 the collected cells are released as the brushes 112 encounter the second flexible membrane 400 as the bristles 114 rotate out of the inner volume. The interaction of the bristles 114 and the edge of the second flexible membrane 400 cleans the bristles 114 and the cells collect on an inner surface of the flexible membrane 202 proximate the edge.

Figure 5:
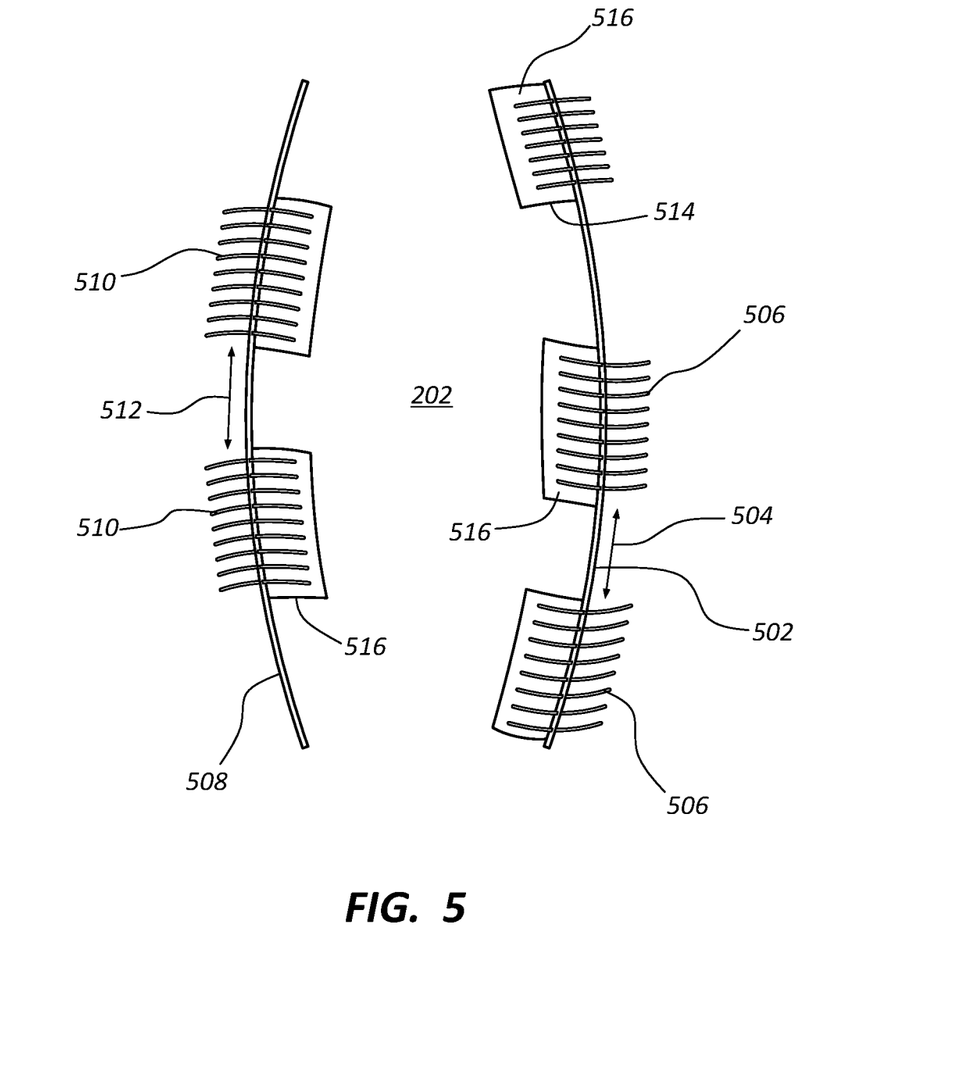
FIG. 5 illustrates a side view of a portion of the cell collection device of FIG. 2.

FIG. 5 illustrates a detailed view of a first strut 502 and an adjacent strut 508 in brush system 100. In this detailed view the brush system 100 has a first plurality of brushes 506 on the first strut 502 and a second plurality of brushes 510 on the second strut 508. The flexible membrane 202 is attached to the first strut 506 at a space 504 between adjacent brushes from among the first plurality of brushes 506. The flexible membrane 202 is also attached to the adjacent strut 508 at a space 512 between adjacent brushes from among the second plurality of brushes 510. In such embodiments the flexible membrane 202 would have an irregular edge 514 with cutouts 516 for each of the brushes.

Figure 6:
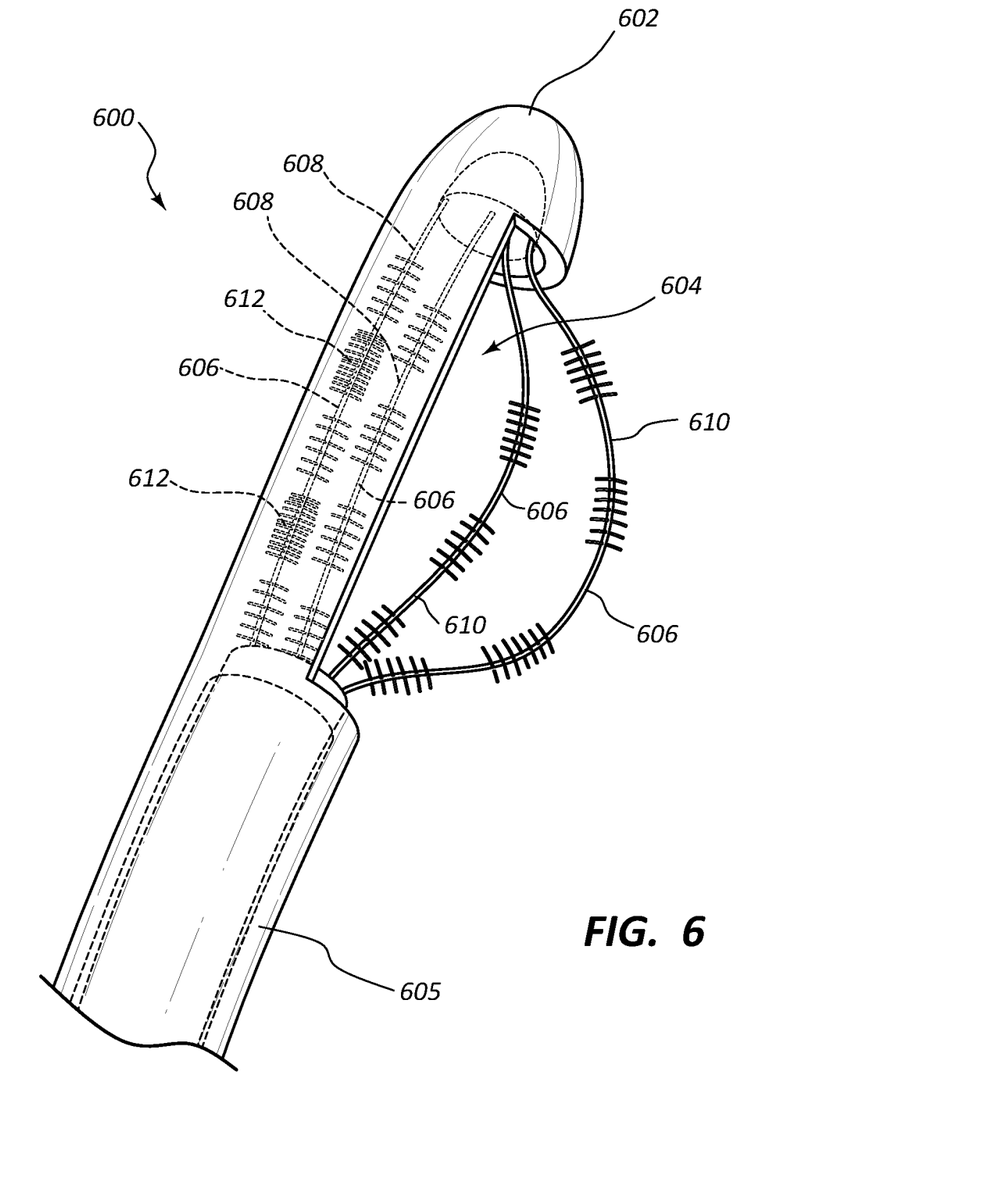
FIG. 6 illustrates an embodiment of a cell collection device with a sheath having a side window.
Figure 7:
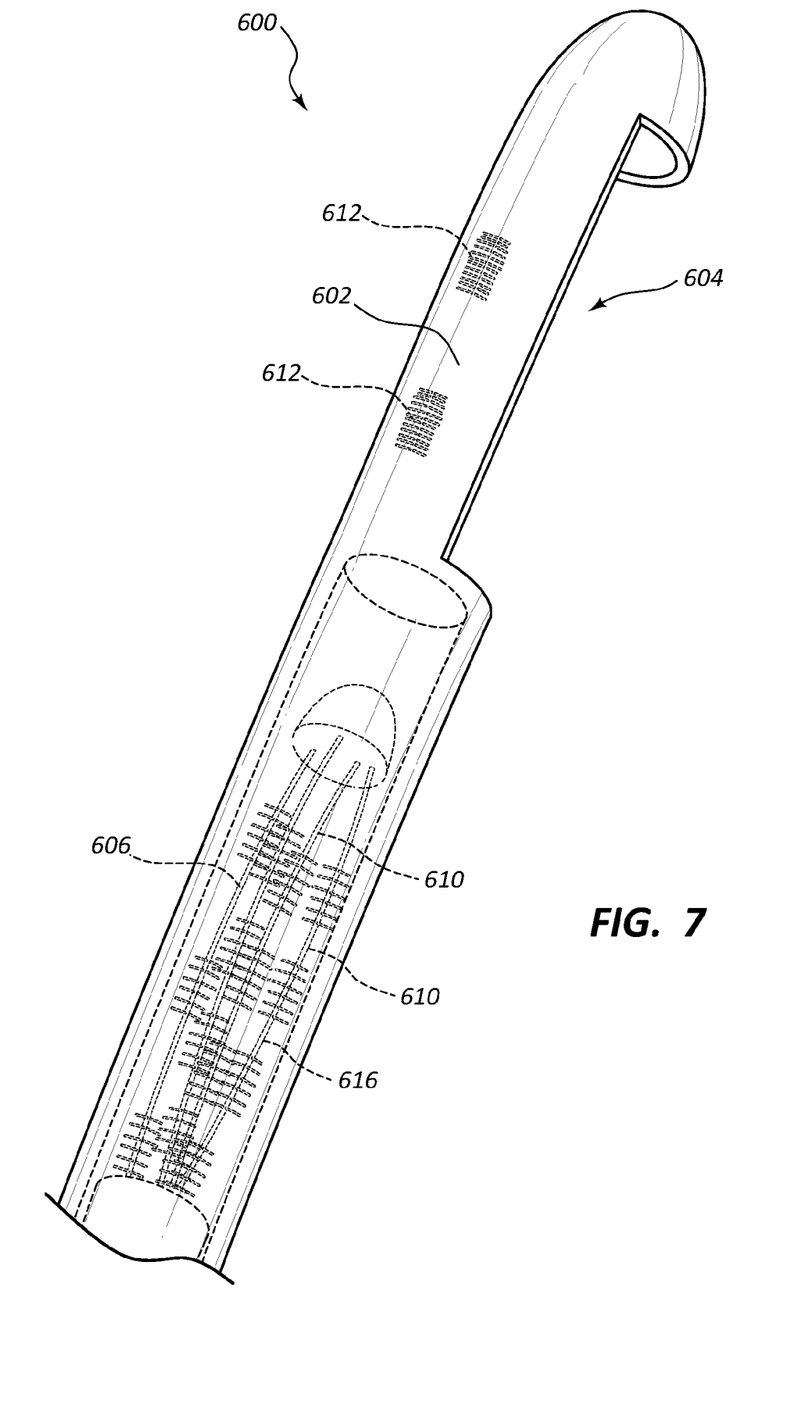
FIG. 7 illustrates the embodiment of FIG. 6, with the sheath extended over the bristles of the cell collection device.

FIG. 6 shows an embodiment of a brush system 600 in which a sheath 602 has a side window 604. The sheath 602 is axially slidable on a first longitudinal member 605 from a first, distal position relative to the first longitudinal member 605 as shown in FIG. 7, to a second position proximal position shown in FIG. 6. In the first position, an inner surface of the sheath 602 constrains an outward bias of a plurality of struts 606. In the second position the sheath 602 covers a second plurality of struts 608 from among the first plurality of struts 606 and does not cover a third plurality of struts 610 from among the first plurality of struts 606. The inner surface of the sheath 602 constrains the second plurality of struts 608 to a high energy state while the side window 604 does not provide a constraint allowing the third plurality of struts 610 to expand outward to their low energy state.

The sheath 602 may have a second plurality of brushes 612 disposed on the inner surface of the sheath 602 opposing the side window 604. The second plurality of brushes 612 may catch captured cells when the longitudinal member 605 is rotated relative to the sheath 602.

It should be understood that various changes and modifications to the presently preferred embodiments described herein will be apparent to those skilled in the art. For example, movement of the sheath is described relative to the longitudinal member. As such, the sheath itself may be moved, or the sheath may be held stationary while the inner longitudinal member is extended or retracted. Such changes and modifications can be made without departing from the spirit and scope of the present invention and without diminishing its intended advantages. It is therefore intended that such changes and modifications be covered by the appended claims.

What is claimed:

1. A cell collection device comprising:
 a longitudinal member having a distal end and a proximal end;
 a plurality of struts extending distally from the distal end of the longitudinal member; at least one brush mounted on one of the struts of the plurality of struts, wherein the at least one brush is rotatable about the strut the at least one brush is mounted on; and
 a sheath slidably disposed about the longitudinal member, the sheath having a lumen with an inner diameter and an inner surface facing the longitudinal member, the sheath having a distal position wherein the inner surface constrains outward radial movement of each strut and a proximal position wherein a portion of at least one strut is unconstrained to move beyond the inner diameter.

2. The cell collection device of claim 1, wherein each strut of the plurality of struts is self-biased to expand a portion of the strut radially.

3. The cell collection device of claim 1, wherein a portion of each strut of the plurality of struts expands radially in response to an axial compressive force.

4. The cell collection device of claim 2, wherein each strut of the plurality of struts is a shaft made of a shape memory material having a high energy state when constrained by the inner surface.

5. The cell collection device of claim 1, further comprising a flexible membrane disposed between adjacent struts.

6. The cell collection device of claim 5, wherein the flexible membrane is comprised of a material selected from the group consisting of nylon reinforced polyurethane, silicone, ultra high molecular weight polyethylene, polyethylene terephthalate, polyethylene, and nylon.

7. The cell collection device of claim 1, further comprising a distal longitudinal member connected to a distal end of the plurality of struts.

8. The cell collection device of claim 1, wherein the plurality of struts are arranged circumferentially at equal radial spacing about a longitudinal axis.

9. The cell collection device of claim 1, wherein the sheath has a side window and the sheath proximal position constrains the outward radial movement of a second plurality of struts from among the plurality of struts and does not constrain the outward radial movement of a third plurality of struts facing the side window.

10. The cell collection device of claim 9, further comprising a second plurality of brushes disposed on the inner surface of the sheath opposing the side window.

11. The cell collection device of claim 5, wherein the flexible membrane is attached to adjacent struts.

12. The cell collection device of claim 11, wherein the flexible membrane is attached to adjacent struts between adjacent brushes.

13. The cell collection device of claim 5, wherein a portion of the flexible membrane extends into at least one brush.

14. The cell collection device of claim 11, wherein the flexible membrane has at least one cut-out complementary to the plurality of brushes.

15. The cell collection device of claim 13, wherein a second portion of the flexible membrane opposite the portion extending into the at least one brush does not extend into a brush.

16. A cell collection device comprising:
a longitudinal member having a distal end and a proximal end;
a plurality of struts extending distally from the distal end of the longitudinal member, at least one brush mounted on one of the struts of the plurality of struts, and a flexible membrane disposed between adjacent struts; and
a sheath slidably disposed about the longitudinal member, the sheath having a lumen with an inner diameter and an inner surface facing the longitudinal member, the sheath having a distal position wherein the inner surface constrains outward radial movement of each strut and a proximal position wherein a portion of at least one strut is unconstrained to move beyond the inner diameter.

17. The cell collection device of claim 16, wherein the flexible membrane is comprised of a material selected from the group consisting of nylon reinforced polyurethane, silicone, ultra high molecular weight polyethylene, polyethylene terephthalate, polyethylene, and nylon.

18. The cell collection device of claim 16, wherein the flexible membrane is attached to adjacent struts.

19. The cell collection device of claim 18, wherein the flexible membrane is attached to adjacent struts between adjacent brushes.

20. The cell collection device of claim 18, wherein the flexible membrane has at least one cut-out complementary to the plurality of brushes.

21. The cell collection device of claim 16, wherein a portion of the flexible membrane extends into at least one brush.

22. The cell collection device of claim 21, wherein a second portion of the flexible membrane opposite the portion extending into the at least one brush does not extend into a brush.

* * * * *